United States Patent [19]

Bertola et al.

[11] Patent Number: 5,075,233

[45] Date of Patent: Dec. 24, 1991

[54] PROCESS FOR THE PREPARATION OF 2-ARYLOXYPROPIONIC ACIDS

[75] Inventors: Mauro A. Bertola, Delft; Marie-José de Smet, Gouda; Arthur F. Marx, Delft, all of Netherlands; Gareth T. Phillips, Kent, United Kingdom

[73] Assignees: Gist-Brocades N.V., Delft; Shell Internationale Research Maatschappij B.V., Den Haag, both of Netherlands

[21] Appl. No.: 212,631

[22] Filed: Jun. 28, 1988

[30] Foreign Application Priority Data

Jul. 2, 1987 [GB] United Kingdom ............... 8715574

[51] Int. Cl.$^5$ .................. C12N 9/18; C12N 9/10; C12N 1/20; C12P 7/62
[52] U.S. Cl. .................................. 435/280; 435/197; 435/193; 435/196; 435/132; 435/135; 435/136; 435/174; 435/252.3; 435/252.5; 435/320.1
[58] Field of Search ............... 435/280, 221, 222, 836, 435/839, 320, 196, 197, 198, 135, 136, 174, 252.3, 252.5, 320

[56] References Cited

U.S. PATENT DOCUMENTS

| | | | |
|---|---|---|---|
| 4,439,524 | 3/1984 | Schutt | 435/813 |
| 4,565,782 | 1/1986 | Bewick | 435/121 |
| 4,568,641 | 2/1986 | Bewick | 435/121 |
| 4,801,537 | 1/1989 | Nagarajan et al. | 435/121 |
| 4,886,750 | 12/1989 | Bertola et al. | 435/830 |
| 4,898,822 | 2/1990 | Asada et al. | 435/121 |

FOREIGN PATENT DOCUMENTS

| | | | |
|---|---|---|---|
| 0133033 | 2/1985 | European Pat. Off. | |
| 0149241 | 7/1985 | European Pat. Off. | 435/221 |
| 0195717 | 9/1986 | European Pat. Off. | |
| 0214569 | 3/1987 | European Pat. Off. | |

OTHER PUBLICATIONS

Ounissi et al., Gene 35:271-278 (1985).
"Asymmetric Hydrolysis of (±)-α-Substituted Carboxylic Acid Esters with Microorganisms", Agricultural and Biological Chemistry, vol. 45, No. 6, (1981), pp. 1389-1392.

Primary Examiner—Robert A. Wax
Assistant Examiner—Stephanie W. Zitomer
Attorney, Agent, or Firm—Fleit, Jacobson, Cohn, Price, Holman & Stern

[57] ABSTRACT

A process is provided for the enrichment in R isomer of an aryloxypropioic acid ester and for the stereoselective hydrolysis of an aryloxypropionic acid ester to form the corresponding aryloxypropionic acid in predominantly S configuration which comprises subjecting an aryloxypropionic acid ester of formula I

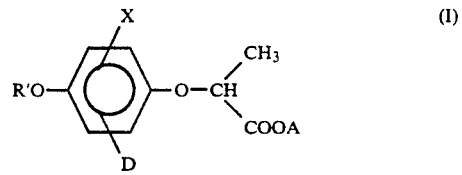

wherein A is an ester residue and preferably an alkyl group, optionally substituted or branched, wherein R' is an optionally substituted aryl or heterocyclic ring system, containing in addition to carbon atoms one or more atoms selected from nitrogen, sulphur and oxygen, this ring system being optionally substituted and wherein B and D are for example a hydrogen or a halogen atom, to the action of a microorganism or substance derived thereof capable of stereoselective hydrolysis of the COOA group to form the corresponding carboxylic acid predominantly is S configuration.

23 Claims, No Drawings

PROCESS FOR THE PREPARATION OF 2-ARYLOXYPROPIONIC ACIDS

The present invention relates to a process for the stereospecific conversion of 2-aryloxypropionic esters to the corresponding carboxylic acid with resulting isomer enrichment in the unconverted ester.

It is known that many biologically active compounds exist as a mixture of stereoisomers. Up to now these mixtures are frequently used as such in agricultural and pharmaceutical applications. Usually the desired biological activity resides mainly in one stereoisomer so that in case of a two stereoisomer mixture the potency of the mixture is reduced to as low as half. However, a major reason for the continued use of mixtures of stereoisomers is that the cost of separation of the stereoisomers exceeds the potential advantage of a possible increase in activity.

Therefore there is a requirement for an industrial scale process giving rise to economically attractive yields for the preparation of a pure enantiomer of 2-aryloxypropionic acids and the object of the invention is to provide such a process.

The present invention provides a process for the enrichment in R isomer of an aryloxypropionic acid ester and for the stereoselective hydrolysis of an aryloxypropionic acid ester to form the corresponding aryloxypropionic acid in predominantly S configuration which comprises subjecting an aryloxypropionic acid ester of formula I

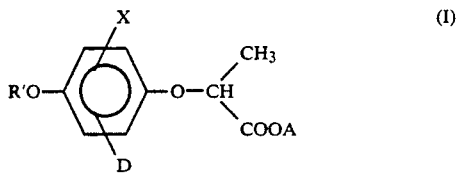

wherein A is an ester residue and preferably an alkyl group, optionally substituted or branched, wherein R' is an optionally substituted aryl or optionally substituted heterocyclic ring system, containing in addition to carbon atoms one or more atoms selected from nitrogen, sulphur and oxygen, this ring system being optionally substituted and wherein X and D are optional substituents, for example a hydrogen or a halogen atom, to the action of a microorganism or substance derived thereof capable of stereoselective hydrolysis of the COOA group to form the corresponding carboxylic acid predominantly is S configurattion. Hereafter the ester predominantly in R configuration is preferably separated from the acid predominantly in S configuration and optionally, the R ester is converted to another ester having R configuration or to the corresponding carboxylic acid having R configuration, the conversion being carried out by methods known per se.

Preferably A is a linear alkyl group of 1 to 6 carbon atoms, optionally substituted or branched with preferably phenyl, methyl or ethyl groups and more preferably is a methyl or an ethyl group.

$R^1$ is an optionally substituted aryl or heterocyclic ring system, this ring system being optionally substituted, for example, with a trifluoromethyl, fluorine, chlorine, bromine, $C_1$–$C_4$ alkyl, methoxy, nitro group.

Suitable compound (I) is fluazifop butyl ester (butyl-2-4-(5-trifluoromethyl-2-pyridyloxy)-phenoxypropionate) or diclofop ethyl ester (ethyl-2-4-(2,4-dichlorophenoxy)phenoxy propionate).

Advantageously according to the process of the present invention 2-aryloxypropionic acid esters of formula (I), or this carboxylic acid itself can be obtained in predominantly the R-configuration, i.e. more than 50% by weight R isomer.

According to a preferred embodiment, the process is carried out by selecting a micro-organism or substance derived thereof, such that the free acid is formed with at least 70% by weight is in the S-configuration, preferably 80% and more preferably 85%.

It is another object of the invention to provide an enzyme which may be advantageously used in the process of the invention.

A number of micro-organisms have now been found which are able stereoselectively to hydrolyse the S-ester of compounds of formula (I). Moreover micro-organisms may be used which are described in the U.S. Pat. No. 4,886,750. This application deals with the preparataion of 2-arylpropionic acids. Experiments show that where racemic mixtures (for example naproxen ester or ibuprofen ester) are used, specifically the S-esters are hydrolysed using certain micro-organisms. However, in the case of phenoxypropionic acids, because of the special arrangements of the groups around the chiral C-atom, one would expect that, as with the naproxen ester, it would be the R-ester that was hydrolysed. It is unexpected that micro-organisms which hydrolyse the esters of S-naproxen would hydrolyse the S-ester of compounds with formula (I).

By the term "micro-organism having the ability for stereoselective hydrolysis" we mean in the present application, micro-organisms such as bacteria, yeasts or fungi. Suitable bacteria are for example from the genus Bacillus and Staphylococcus, a suitable yeast is for example from the genus Pichia and a suitable fungus is for example from the genus Debaromyces.

Use may be made of mutants derived from these microorganisms as well.

Use may also be made of micro-organisms, which have obtained their ability for stereoselective hydrolysis of ester (I) by the introduction of novel genetic material.

This can be accomplished by transferring the cloned gene encoding a substance responsible for the stereoselective hydrolysis, an esterase enzyme, from any of the screened micro-organisms to another micro-organism, particularly to *Escherichia coli*. Other micro-organisms which may be transformed are of the genus Saccharomyces, Kluyveromyces, Bacillus, Aspergillus, Escherichia, Pseudomonas and Streptomyces. Cloned genes may be selected for their ability to encode an enzyme capable of hydrolyzing an ester such as βnaphthyl-acetate, naproxen ester or a compound of the formula (I). Alternatively they may be selected by cross-hybridization with an already selected gene encoding an esterase. The latter choice is based on the observation that related micro-organisms show homology in the DNA sequence of corresponding enzymes (Ihara et al., 1985, J. Biochem. 98, p. 95) and on our own observation that plasmid pNAPT-7 (see Example 11 of U.S. Pat. No. 4,886,750 exhibits cross-hybridization with chromosomal DNA derived from other Bacillus species. In addition, this invention comprises a method for the introduction of multiple and/or modified gene copies encoding the esterase into a micro-organism with the advantage of increasing the activity of the micro-organism, or the substance derived thereof, in the hydrolysis of ester (I). This micro-organism may be for example *Bacillus subtilis*.

The micro-organisms may advantageously be immobilized, for example on a polymer gel. This can be done with living, resting and/or killed cells, but alternatively with an esterase enzyme, which may be purified to a certain extent if a higher specific activity is needed.

Therefore by the term "micro-organisms or substance derived thereof" we mean the micro-organisms, killed, alive or resting cells or extracts therefrom, optionally concentrated or purified. It is found that cell hydrolysates or enzymes (preparations) derived or isolated from the living cells or killed cells may convert the S-isomer of compound (I) under suitable conditions. For example, intracellular or extracellular enzymes can be obtained from such microorganisms. The conversion into S-isomer of the free carboxylic acid may take place in suitable buffers as well as in physiological salts. After being stored the induced cells are found to be directly capable to convert the ester (I) into the S-isomer of the free carboxylic acid.

Cultures of species Bacillus which may be used in this invention include cultures of *Bacillus licheniformis* (a sample of this species is deposited with the ATCC under the accession number 11945), *Bacillus subtilis*, preferably *Bacillus subtilis* Thai I-8 (a sample of this species is deposited with the CBS under the accession number 679.85) and Bacillus species Nap 4M (a sample of this species is deposited with the CBS under the accession number 342.87). Cultures of species Staphylococcus which may be used in this invention include cultures of *Staphylococcus aureus* (a sample of this species is deposited with the CBS under the accession number 341.87), *Staphylococcus aureus* Nap 2-5 (a sample of this species is deposited with the CBS under the accession number 340.87). Cultures of species Pichia which may be used in this invention include cultures of *Pichia farinosa* (a sample of this species is deposited with the IFO under the accession number 0534). Cultures of species Debaromyces which may be used in this invention include cultures of species *Debaromyces hansenii* (a sample of this species is deposited with the IFO under the accession number 0034). Strain Nap 10M may be used in this invention, a sample is deposited with the CBS under the accession number 805.85).

The address for American Type Culture Collection (ATCC) is 12301 Parklawn Drive, Rockville, MD 20852. The address for Institute For Fermentation, Osaka (IFO) is 17-85, Juso-Honmachi 2-Chome, Yodogawa-ku, Osaka 532, Japan. The address for Centraabureau Voor Schimmelcultures (CBS) is P.O. Box 273, 37 BAARN, The Netherlands.

According to a preferred embodiment of the present invention, a micro-organism having the ability to convert compound (I) into the corresponding free carboxylic acid having at least 70% by weight in S-configuration, may be cultured for about 0.5 to 10 days. The cells may be then be suspended in a liquid nutrient medium and the compound (I) then subjected to the action of the cells. Alternatively the cells may be killed for example suspended in a lysis medium, and compound (I) is then subjected to the action of substances derived from the cells.

After the above-mentioned cultivation for about 0.5 to 10 days, the cells may be isolated from the culture medium before suspending the cells in the liquid nutrient medium or suspending the cells in a lysis medium.

To grow the micro-organisms used for the selective hydrolysis of compound (I), ordinary culture media containing an assimilable carbon source (for example glucose, lactate, sucrose, etc.), a nitrogen source (for example ammonium sulphate, ammonium nitrate, ammonium chloride, etc.), with an agent providing an organic nutrient source (for example yeast extract, malt extract, peptone, meat extract, etc.) and an inorganic nutrient source (for example phosphate, magnesium, potassium, zinc, iron and other metals in trace amounts) may be used.

A Jap medium, optionally enriched with one or more ingredients, may be used as a suitable culture medium. A Jap medium of the following composition may be used: soybean flour (30 g/l), sodium nitrate (7.5 g/l), ferrous sulphate. $7H_2O$ (0.28 g/l), sodium citrate (6 g/l) and fructose (12.5 g/l), the pH adjusted to 7.2. Before use the medium should be sterilized e.g. for 20 minutes at 120° C.

Another preferred culture medium is a TSB-medium 2X, optionally enriched with one or more ingredients. A medium consisting of 60 g/l trypticase soy broth (Oxoid ®) may be used. Before use the medium should be sterilized e.g. for 20 minutes at 120° C. Another preferred medium is 2xTY optionally enriched with one or more ingredients. A medium consisting of Tryptone (Difco ®) 30 g/l, Yeast extract (Difco ®) 20 g/l, NaCl 3 g/l, $(NH_4)_2HPO_4$ 1 g/l and $(NH_4)_2SO_4$ 1 g/l at pH 6.8 can be used. Before use the medium should be sterilized e.g. for 30 minutes at 110° C. A more preferred culture medium is a skimmed milk medium optionally enriched with one or more ingredients. A skimmed milk medium of the following composition may be used: 10% skimmed milk from skimmed milkpowder, which should be sterilized e.g. for 30 minutes at 110° C. before use.

As enrichments to the skimmed milk medium for example 0.5% lactate or PSIII salts or combinations thereof may be used. PSIII salt medium of the following composition may be used: potassium dihydrogen phosphate (2.1 g/l), ammonium monohydrogen phosphate (1.0 g/l), ammonium sulphate (0.9 g/l), potassium chloride (0.2 g/l), sodium citrate (0.29 g/l), calcium sulphate. $2H_2O$ (0.005 g/l), magnesium sulphate. $7H_2O$ (0.2 g/l), ammonium ferrous sulphate. $6H_2O$ (2.5 mg/l), zinc sulphate. $7H_2O$ (0.5 mg/l), manganese chloride. $4H_2O$ (0.3 mg/l), copper sulphate. $5H_2O$ (0.15 mg/l), cobalt chloride. $6H_2O$ (0.15 mg/l), ortho-boric acid (0.05 mg/l), sodium molybdate. $2H_2O$ (0.055 mg/l) and potassium iodide (0.1 mg/l), the pH adjusted at 6.8. Before use the PSIII salt medium should be sterilized e.g. for 20 minutes at 120° C.

A temperature of 0° to 45° C. and a pH of 3.5 to 9 is preferably maintained during the growth of the micro-organisms. More preferably the micro-organisms are grown at a temperature of 20° to 37° C. and a pH of 5 to 9.

The aerobic conditions required during the growth of the micro-organisms may be provided according to any of the well-established procedures, provided that the supply of oxygen is sufficient to meet the metabolic requirement of the micro-organisms. This is most conveniently achieved by supplying oxygen, suitably in the form of air and optionally at the same time shaking or stirring the reaction liquid. During the conversion of ester (I) into the free carboxylic acid the micro-organisms might be in a growing stage using an abovementioned ordinary culture medium or might be preserved in any system (medium or buffer) preventing degradation of enzymes.

During the conversion of ester (I) into the free carboxylic acid, an ordinary culture medium may be used containing an assimilable carbon source when required (for example glucose, lactate, sucrose, etc.), a nitrogen source when required (for example ammonium sulphate, ammonium nitrate, ammonium chloride, etc.), with an agent providing an organic nutrient source when required (for example yeast extract, malt extract, peptone, meat extract, etc.) and an inorganic nutrient source when required (for example phosphate, magnesium, potassium, zinc, iron and other metals in trace amounts).

Preferably, during the conversion of ester (I) into the free carboxylic acid, a Jap medium (as described above) optionally enriched with one or more ingredients may be used. More preferably a skimmed milk medium (as described above) optionally enriched with one or more ingredients is used.

The micro-organisms can be kept in the non-growing stage, for example by exclusion of the assimilable carbon source or by exclusion of the nitrogen source. A temperature of 0° to 45° C. and a pH of 3.5 to 9 is preferably maintained during this hydrolysis stage.

During the hydrolysis stage the micro-organisms are preferably kept at a temperature of 20° to 37° C. and a pH of 5 to 8. The aerobic conditions required during this stage can be provided according to any of the well-established procedures, provided that the supply of oxygen is sufficient to meet the metabolic requirement of the micro-organisms. This is most conveniently achieved by supplying oxygen, suitably in the form of air and optionally, at the same time, shaking or stirring the reaction liquid. The free caroboxylic acid produced by can be separated and ester (I) enriched in R configuration can be recovered and purified, and if desired, converted into another ester or the free acid having R configuration, according to any of the procedures known per se for such products.

The micro-organisms can be kept on agar slants, frozen in 50% glycerol or lyophilised. If required, precultures of these micro-organisms can be made according to any of the well-established procedures, for example the micro-organisms can be incubated in bouillon or in BHI for 24 hours at 30° C. in a rotary shaker. A bouillon medium of the following composition may be used: Lab Lemco L 29 (meat extract, Oxoid ®) (9 g/l), Bactopepton (10 g/l) and sodium chloride (5 g/l), the pH adjusted to 7.6. Before use this medium should be sterilized e.g. for 20 minutes at 120° C.

A BHI (brain-heart infusion) medium containing 0.037 g/l BHI (Oxoid ®), the pH adjusted to 7.0, may be used. Before use this medium should be sterilized e.g. for 20 minutes at 120° C.

A YEPD medium may be used of the following composition: 20 g/l bactopepton, 10 g/l yeast extract, 20 g/l glucose. Before use this medium should be sterilized e.g. for 30 minutes at 110° C.

The enzyme capable of the hydrolysis of ester (I) derived from Bacillus Thai I-8 has been characterized in U.S. Pat. No. 4,886,750. It has been found that the esterase activity is not related to the lipase activity present in the micro-organism. In fact the low amount of hydrolysis of the "wrong" isomer of the ester appeared to be mainly due to the contaminating lipase activity of the Bacillus strain. The purified esterase of Thai I-8 has a significantly higher enantiomeric selectivity than the total cell lysate of Bacillus.

The E. coli/pNAPT-7 and Bacillus/pNAPT-7, both strains having a plasmid containing the Thai I-8 esterase, produce a significant amount of esterase. Surprisingly the protein which possesses the esterase activity as confirmed by SDS-PAGE, HPLC-SEC and isoelectric-focusing is by far the protein with the highet concentration in the cell lysate of the micro-organisms.

Although it is known that gene cloning can improve the expression level of an enzyme, the amount of enhancement in the case of esterase is very surprising. Very often problems as incorrect folding, protein degradation and intracellular precipitation are encountered when cloning the gene for an enzyme (Harris, T.J.R., 1983, Genetic Engineering 4, Academic Press). Unexpectedly none of these problems seem to occur when cloning esterase genes.

A further aspect of the present invention provides a herbicidal composition comprising a herbicidally active salt, acid or ester in predominantly R or predominantly S form obtained by the process of the invention, together with an inert diluent or carrier.

The present invention will be further described with reference to the following examples, without restricting the scope of the present invention to these examples.

EXAMPLE 1

Three bacteria and one fungus were precultured in BHI (the bacteria) or YEPD (the fungus) for 24 hours at 30° C. and then inoculated in 10% skimmed milk. Each strain was inoculated 5× in 100 ml kept in 500 ml baffle flasks and incubated for 48 or 72 hours at 30° C. Thereafter 1.25M Tris/HCl buffer, pH 8.0, to a final concentration of 50 mM, was added to the cultures as well as 40 mg racemic Fluazifop butyl ester dissolved in soyoil (200 mg ester/ml soyoil) and the cultures were further incubated for 24 hours. After this incubation period, the cultures were extracted with ethyl acetate and the remaining ester and acid formed were isolated and purified using a silica gel column.

The optical rotation of the isolated ester and acid was then determined.

The enantiomeric purity of the ester and acid was further established by HPLC on a Bakerbond DNBPG (Dinitrobenzoyl phenylglycine) covalent column after transesterification or esterification of respectively the ester and the acid using $BF_3$/MeOH.

The results are presented in Table 1.

TABLE 1

| | Resolution of Fluazifop butyl ester | | | | | |
|---|---|---|---|---|---|---|
| Strains | Ester* isolated mg | $[\alpha]_D^{rt}$ $CHCl_3$ | enantiomeric purity | Acid isolated mg | $[\alpha]_D^{rt}$ $CHCl_3$ | enantiomeric purity |
| Staphylococcus aureus Nap 2-5 (CBS 340.87) | 52 | +10.7 | R: 70% | 50 | −5.2 | S: 79% |
| Bacillus | 72 | +3.6 | R: 59% | 34 | −7.0 | S: 65% |

TABLE 1-continued

| | Resolution of Fluazifop butyl ester | | | | | |
|---|---|---|---|---|---|---|
| Strains | Ester* isolated mg | $[\alpha]_D^{rt}$ CHCl$_3$ | enantiomeric purity | Acid isolated mg | $[\alpha]_D^{rt}$ CHCl$_3$ | enantiomeric purity |
| spec. Nap 4M (CBS 342.87) | | | | | | |
| Bacillus licheniformis (ATCC 11945) | 72 | +19 | R: 93% | 56 | −15.5 | S: 85% |
| Debaromyces hansenii (IFO 0034) | 88 | −8.1 | R: 70% | 33 | −14.9 | S: 85% |

*Total ester input ca. 200 mg.

EXAMPLE 2

Five organisms were pregrown as described in Example 1 and inoculated in 25 ml of 10% skimmed milk kept in 100 ml baffle flasks. After 48 hours growth at 30° C. about 16 mg racemic diclofop ethyl ester dissolved in soyoil was added to the cultures and they were further incubated for 24 hours (no Tris/HCl buffer was added in this experiment).

After the incubation period the cultures were acidified with H$_3$PO$_4$ to pH 4.0 and extracted with 2 ml of methylene dichloride. The remaining ester and acid formed were isolated and analysed with HPLC. The ester was sometimes analysed without transesterification. The acid was always first esterified with BF$_3$/MeOH.

The results are presented in Table 2.

TABLE 2

| | Resolution of diclofop ethyl ester | | | |
|---|---|---|---|---|
| Strains | Ester* found g/l | enantiomeric purity | Acid found g/l | enantiomeric purity |
| Staphylococcus aureus Nap 2-5 (CBS 340.87) | 0.23 | R: 99% | 0.29 | S: 82% |
| Bacillus spec. Nap 4M (CBS 342.87) | 0.22 | R: 79% | 0.26 | S: 74% |
| Bacillus licheniformis (ATCC 11945) | 0.23 | R: 94% | 0.24 | S: 90% |
| Debaromyces hansenii (IFO 0034) | 0.34 | R: 58% | 0.08 | S: 84% |
| Bacillus subtilis Thai I-8 (CBS 679.87) | 0.16 | R: 100% | 0.36 | S: 68% |
| Pichia farinosa (IFO 0534) | 0.30 | R: 75% | 0,10 | S: 89% |

*Total ester imput ca. 0.8 g/l
The values mentioned are the mean of a duplicate result.

EXAMPLE 3

Five organisms were pregrown as described in Example 1 and inoculated in 25 ml of 10% skimmed milk kept in 100 ml baffle flasks. After 48 hours growth at 30° C. about 10 mg racemic diclofop methyl ester dissolved in soy oil were added to the cultures and they were further incubated for 24 hours (no Tris/HCl buffer was added in this experiment).

After the incubation period the cultures were acidified with H$_3$PO$_4$ to pH 4.0 and extracted once with 25 ml of methylene dichloride. The remaining ester and acid formed were isolated and analysed with HPLC.

The ester could be analysed without transesterification. The acid was first esterified with BF$_3$/MeOH.

The results are presented in Table 3.

TABLE 3

| | Resolution of diclofop methyl ester | | | |
|---|---|---|---|---|
| Strain | ester* found g/l | enantiomeric purity | acid found g/l | enantiomeric purity |
| Bacillus licheniformis (ATCC 11945) | 0.07 | R: 94 | 0.18 | S: 85 |
| Pichia farinosa (IFO 0534) | 0.08 | R: 85 | 0.13 | S: 79 |
| Staphylococcus aureus (CBS 340.87) | 0.04 | R: 78 | 0.03 | S: 88 |
| Staphylococcus aureus (CBS 341.87) | 0.12 | R: 69 | 0.13 | S: 67 |
| Strain Nap 10M (CBS 805.85) | 0.11 | R: 62 | 0.08 | S: 69 |

*Total ester input ca. 0.4 g/l.

EXAMPLE 4

Three organisms were pregrown as described in Example 1 and inoculated in 25 ml of 10% skimmed milk kept in 100 ml baffle flasks. After 48 hours growth at 30° C. about 10 mg racemic fenoxaprop ethyl ester dissolved in soy oil were added to the cultures and they were further incubated for 24 hours (no Tris/HCl buffer was added in this experiment).

After the incubation period the cultures were acidified with H$_3$PO$_4$ to pH 4.0 and extracted once with 25 ml of methylene dichloride. The remaining ester was isolated and analysed with HPLC.

The results are presented in Table 4.

TABLE 4

| | Resolution of fenoxaprop ethyl ester | |
|---|---|---|
| Strain | ester* found g/l | enantiomeric purity |
| Debaromyces hansenii (IFO 0034) | 0.09 | R: 84 |
| Pichia farinosa (IFO 0534) | 0.10 | R: 81 |
| Staphylococcus aureus (CBS 340.87) | 0.20 | R: 80 |

*Total ester input ca. 0.4 g/l.

EXAMPLE 5

The hydrolysis of diclofop ethyl ester and diclofop methyl ester by the Thai I-8 esterase (cloned in and isolated from Bacillus 1-85/pNap T7, CBS 673.86) was performed in 10 ml reaction medium kept in 100 ml flasks. The reaction medium consisted of enzyme extract ($10^{-3}$ units/ml), 0.1M MOPS buffer pH 7.5, BSA (2 mg/ml), racemic diclofop ethyl ester (0.2 mg/ml) and Tween-80 (2% (v/v)). The mixture was incubated for 2 hours at 30° C. on a rotary shaker. After the incubation period the mixture was extracted with methylene dicloride and the remaining ester and acid formed analysed with HPLC. The ester and the acid were first esterified with $BF_3$/MeOH. The results are presented in Tables 5 and 6.

TABLE 5

Resolution of diclofop ethyl ester by Thai I-8 esterase.

| enantiomeric purity of | |
|---|---|
| ester | acid |
| R: 66% | R: 0% |
| S: 34% | S: 100% |

TABLE 6

Resolution of diclofop methyl ester by Thai I-8 esterase.

| enantiomeric purity of | |
|---|---|
| ester | acid |
| R: 60% | R: 0% |
| S: 40% | S: 100% |

We claim:

1. A process for the enrichment in R isomer of an aryloxypropionic acid ester and for the stereoselective hydrolysis of an aryloxypropionic acid ester to form the corresponding aryloxypropionic acid in predominantly S configuration which comprises subjecting an aryloxypropionic acid ester of formula I

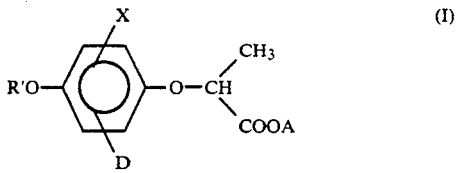

wherein A is an optionally substituted or branched alkyl group, wherein R' is an optionally substituted aryl or optionally substituted heterocyclic ring system, containing in addition to carbon atoms one or more atoms selected from nitrogen, sulphur and oxygen, and wherein X and D are optional substituents, to the action of a microorganism or substance derived therefrom capable of stereoselective hydrolysis of the COOA group to form the corresponding carboxylic acid predominantly in S configuration.

2. A process according to claim 1, wherein the ester predominantly in R configuration is separated from the acid predominantly in S configuration.

3. A process according to claim 1, wherein at least 70% by weight of the carboxylic acid is formed in the S-configuration.

4. A process according to claim 1, wherein predominantly the R form of fluazifop butyl ester or diclofop ethyl ester is isolated.

5. A process according to claim 1, wherein the microorganism is used in immobilized form either as a living cell, as a killed cell or as a resting cell.

6. A process according to claim 1 wherein a substance is released from the microorganism and used to stereoselectively convert compound (I) into the corresponding carboxylic acid in S configuration.

7. A process according to claim 1, wherein said micro-organism is a bacterium, a yeast or a fungus.

8. A process according to claim 7, wherein said micro-organism is a bacterium belonging to the genus Bacillus or Staphylococcus, a yeast belonging to the genus Pichia, or a fungus belonging to the genus Debaromyces.

9. A process according to claim 1 wherein said micro-organism is a micro-organism transformed with a DNA fragment encoding esterase.

10. A process according to claim 9 wherein the DNA fragment is derived from any Bacillus species.

11. A process according to claim 10 wherein the DNA fragment is derived from Bacillus subtilis.

12. A process according to claim 11 wherein the DNA fragment is inserted into a plasmid.

13. A process according to claim 12 wherein the plasmid is pNAPT-7 or pNAPT-8.

14. A process according to claim 9 wherein the micro-organism used is *Escherichia coli*.

15. A herbicidally active acid salt or ester in predominantly R or predominantly S configuration when produced by a process according to any one of the preceding claims.

16. A herbicidal composition containing at least one compound according to claim 17 together with an inert carrier or diluent.

17. Enzyme, having the ability for stereoselective hydrolysis of the ester (I) as defined in claim 1 into the corresponding carboxylic acid having predominantly the S-configuration.

18. A process according to claim 1 wherein an enzyme, having the ability for stereoselective hydrolysis of the ester (I) as defined in claim 1 into the corresponding carboxylic acid having predominantly the S-configuration is used, whereafter the resulting acid enriched in S-isomer is substantially separated from the ester (I) enriched in R-isomer.

19. A micro-organism selected from the group consisting of *Bacillus species* Nap 4M (CBS 342.87) and *Staphylococcus aureus* Nap 2-5 (CBS 340.87) or mutants and variants thereof.

20. A process according to claim 1, wherein the ester predominantly in R configuration is separated from the acid predominantly in S configuration, and then the R ester is converted to another ester having R configuration or to the corresponding carboxylic acid having R configuration.

21. A process according to claim 1, wherein A is a linear alkyl group of one to six carbon atoms.

22. A process according to claim 8, wherein said micro-organism is a member selected from the group consisting of *Bacillus licheniformis, Bacillus subtilis* and *Staphylococcus aureus*, and mutants thereof.

23. A process according to claim 8, wherein said micro-organism is a member selected from the group consisting of *Bacillus licheniformis* (ATCC 11945), *Bacillus subtilis* Thai I-8 (CBS 679.85), Bacillus species Nap 4-M (CBS 342.87), *Staphylococcus aureus* (CBS 341.87), *Staphylococcus aureus* Nap 2-5 (CBS 340.87), *Pichia farinosa* (IFO 0534), *Debaromyces hansenii* (IFO 0034), and strain Nap 10M (CBS 805.85), and mutants thereof.

* * * * *